(12) United States Patent
Neuberger

(10) Patent No.: US 6,355,054 B1
(45) Date of Patent: Mar. 12, 2002

(54) LASER SYSTEM FOR IMPROVED TRANSBARRIER THERAPEUTIC RADIATION DELIVERY

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/435,229

(22) Filed: Nov. 5, 1999

(51) Int. Cl.$^7$ ................................................. A61N 5/00
(52) U.S. Cl. .............................. 607/89; 606/9; 604/20
(58) Field of Search .......................... 604/19–21; 606/2, 606/3, 9–15; 607/88, 89

(56) References Cited

U.S. PATENT DOCUMENTS

| 5,000,752 A | 3/1991 | Hoskin et al. |
| 5,226,907 A | 7/1993 | Tankovich |
| 5,454,807 A | 10/1995 | Lennox et al. |
| 5,735,844 A | 4/1998 | Anderson et al. |
| 5,749,868 A | 5/1998 | Furumoto |

*Primary Examiner*—Michael Peffley
(74) *Attorney, Agent, or Firm*—Bolesh J. Skutnik; BJ Associates; A. L. Robitaille

(57) ABSTRACT

The present invention describes a system and method to improve radiation delivery through a barrier that may be encountered during therapeutic laser procedures, particularly where the objective of treatment is to produce thermal damage or alterations to subsurface tissue constituents without destroying or altering the overlying barrier. To achieve this result, a bio-compatible fluid is preoperatively administered to the tissue. The bio-compatible fluid is a light-scattering fluid that will scatter light primarily at the desired site thereby achieving a more uniform, enhanced heating over a relatively large treatment area. In addition, a second fluid, a dispersion fluid, can be added to the tissue to function in distributing the light scattering fluid throughout the treatment site. Laser radiation is then administered, through micro pores created for example by a device such as a micro-needle patch, into the treatment site. When a micro-needle patch is employed to deliver the fluid and the radiation, it can be a single patch for both functions, or a separate patch for each function.

18 Claims, 6 Drawing Sheets

LASER SYSTEM FOR IMPROVED TRANSBARRIER THERAPEUTIC RADIATION DELIVERY

BACKGROUND OF THE INVENTION

1. Field of the Invention

The present invention describes a method to enhance radiation delivery through a barrier that may be encountered during therapeutic laser procedures, particularly where the objective of treatment is to obtain uniform sub-barrier heating and to effect thermal damage to subsurface tissue constituents without destroying or altering the overlying barrier.

2. Information Disclosure Statement

Since its invention in 1960, the laser has found niches in both diagnostic and therapeutic medical applications. Lasers have become widely accepted for treating vascular lesions, comprising enlarged or ectatic blood vessels, pigmented lesions, and tattoos. More recent additions to the list of aesthetic laser treatments include abatement of wrinkles, scars and other blemishes, removal of unwanted hair, creation of skin pockets during hair transplantation surgery and shrinkage of varicose veins. In the above-stated procedures it is necessary to use a sufficient dose of light to irradiate subsurface tissue constituents to achieve the desired clinical effects. However, the delivery of radiation to the appropriate treatment site can be problematic because excessive absorption at the stratum corneum often results in epidermal damage and scattering in the dermal region often results in inadequate heat generation at the treatment site.

Various solutions have been proposed to eliminate the above-stated complications. Generally, the solutions concentrate on increasing the absorption at the treatment site or facilitating transmission through the epidermis.

For example, U.S. Pat. No. 5,226,907 describes a device and method for light-induced hair removal that involves placing an absorptive substance at the treatment site and exposing that substance to the proper wavelength of light. The light-absorbing substance is allowed to migrate at least part-way into the follicle or treatment site. The excess light-absorbing substance is then removed and the area is irradiated to destroy, modify or stimulate the treatment site. However, it is difficult to get the light-absorbing substance or chromophore deep enough into the treatment site to effect destruction, modification, or stimulation of subsurface tissue constituents. Further, this technique results in substantial energy being applied to and absorbed by the epidermis and other skin layers in the region being treated, with significantly reduced energy reaching the treatment area. Therefore, it is difficult to achieve and sustain the critical core temperature that is necessary to destroy, modify or stimulate without damaging the surrounding tissue and without causing pain and injury to the patient.

Whereas, U.S. Pat. No. 5,454,807 describes a device that can facilitate transmission of light through the epidermis. Specifically, a conduit is constructed to deliver a flow of coolant to the surface of a treatment site. Generally cryogen has been used as a coolant to protect the epidermis because the liquid-vapor phase transition of cryogen has been shown to provide a mechanism for selectively cooling the skin. Specifically, the liquid-phase transition of cryogen creates a boundary layer which creates a heat sink below the surface of the skin that can rapidly remove trapped heat before, during, and after laser exposure to protect the epidermis from thermal damage. However, this technique can be counterproductive if a heating effect is desired in the epidermal or upper dermal region because the treatment site will also be cooled and as a result may remain resistant to photothermolysis.

U.S. Pat. No. 5,749,868 describes another method to facilitate transmission of light through the epidermis by using light in the near infrared region to effect a decrease in the ratio of melanin to hemoglobin absorption in the treatment of blood vessels. The method described is, however, limited. First, the method does not provide a way to get through the epidermis. What the invention provides is merely a way to decrease the negative skin-surface side effects (such as hyper-pigmentation) resulting from the treatment. It is evident from the patent description that melanin absorption still occurs at the described treatment wavelengths therefore, some amount of surface damage will still be present, only minimized. The described invention combines the commonly accepted idea that increased penetration can be obtained by using longer wavelengths of light with the use of light in the specific near-IR wavelengths that increase hemoglobin absorption. Second, the invention described addresses exclusively the ratio of melanin to hemoglobin absorption and is therefore limited to blood vessel treatment and is limited in its application.

U.S. Pat. No. 5,000,752 describes a method for transdermal laser delivery through the insertion of an array of surgical needles into a treatment tissue, preventing damage to the skin surface. The needles are attached in a fixed pattern on a flexible pad that allows the entire array to be inserted at one time. However, there are a couple of drawbacks to this invention. First, treatment with the device is painful for the patient. The stratum corneum, or the outermost $10–15\mu$ of skin, has no nerve endings. Penetration below that layer, however, causes pain. The device is described as having delivery needles greater in length than the depth of the stratum corneium. Second, the needles employed in the invention are intrusive and increase the chance of infection. The larger the bore of the delivery needle, the larger the entry hole and the greater the chance that microorganisms might be introduced into the site. Third, the invention describes an array of very detailed delivery needles with adjustable, specialized tips. The device must therefore be expensive to manufacture and purchase. Practical application of the invention can be hindered by its cost.

In another example, U.S. Pat. No. 5,735,844 describes a method of improving laser delivery by inserting a needle-like element into the follicle to facilitate light energy reaching the appropriate treatment site. However, this procedure is very painful. On the other hand, if the irradiation source is not inserted into the follicle, it is difficult to get sufficient energy to achieve and sustain the critical core temperature that is necessary to destroy, modify or stimulate without also causing significant damage to the surrounding tissue and thus causing pain and injury to the patient.

An ideal device would enable the irradiation source to be inserted into the treatment site without pain to the patient to improve heat generation at the treatment site and to facilitate the transmission of light energy through the epidermis. Thus, a device and method are needed that will improve transdermal laser delivery without the complications associated with the prior art.

OBJECTS AND SUMMARY OF THE PRESENT INVENTION

It is an object of the present invention to provide a system and method for improved transbarrier laser delivery to the appropriate treatment site without the complications associated with the prior art.

It is another aim of the present invention to insert the irradiation source, transbarrierly, into the treatment site without pain to the patient to facilitate radiation delivery through the epidermis.

It is a further aim of the present invention to employ pre-treatment methods to further enhance heat generation at the treatment site.

Briefly stated, the present invention describes a system and method to improve radiation delivery through a barrier that may be encountered during therapeutic laser procedures, particularly where the objective of treatment is to produce thermal damage or alterations to subsurface tissue constituents without destroying or altering the overlying barrier. To achieve this result, a bio-compatible fluid is preoperatively administered to the tissue. The bio-compatible fluid is a light-scattering fluid that will scatter light primarily at the desired site thereby achieving a more uniform, enhanced heating over a relatively large treatment area. In addition, a second fluid, a dispersion fluid, can be added to the tissue to function in distributing the light scattering fluid throughout the treatment site. Laser radiation is then administered, through micro pores created for example by a device such as a micro-needle patch, into the treatment site. When a micro-needle patch is employed to deliver the fluid and the radiation, it can be a single patch for both functions, or a separate patch for each function.

The above and other objects, features, and advantages of the present invention will become apparent from the following detailed description read in conjunction with the accompanying drawings.

DETAILED DESCRIPTION OF THE PREFERRED EMBODIMENTS

The present invention describes a system and method of use that controls the degree and spatial distribution of heating in the epidermis and dermis to achieve and sustain the critical core temperature that is necessary to ablate or stimulate the treatment site. The invention relates to therapeutic procedures where the objective of treatment is to produce irreversible thermal damage to subsurface tissue constituents without destroying or altering the outer barrier. Although most examples refer to an epidermal barrier that must be penetrated, this should not be taken to imply that the present invention is limited to enhancing radiation delivery only through the epidermis. The present invention may be used to enhance radiation delivery through any barrier that is encountered. Other suitable variations of the present invention may include, but are not limited to delivering laser energy through soft tissue in the oral cavity or through arterial or venal walls.

Figure 1:
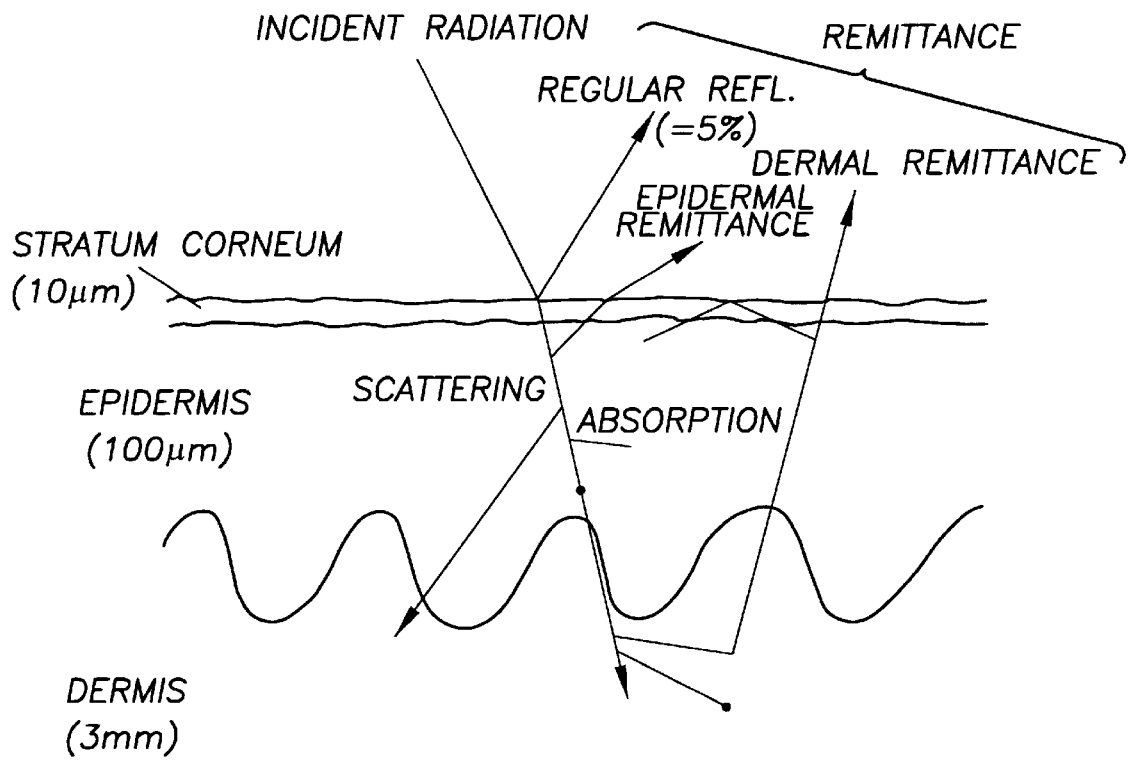
FIG. 1 illustrates the various laser-tissue interactions that can occur during laser therapy.

FIG. 1 illustrates the various laser-tissue interactions that can occur during laser therapy. At near-normal (nearly perpendicular) incidence, a small fraction of an incident radiation is reflected due to the change in refractive index between air ($N_D$=1.0) and stratum corneum ($N_D \cong 1.55$). For normally incident radiation, this regular reflectance of an incident beam from normal skin is typically between 4% and 7% over the entire spectrum from 250–3000 nm. This same air-tissue optical interface also causes internal reflection of diffuse, back-scattered radiation. Within any of the layers of skin, the 93% to 96% of the incident radiation not returned by regular reflectance may be absorbed or scattered.

Figure 2:
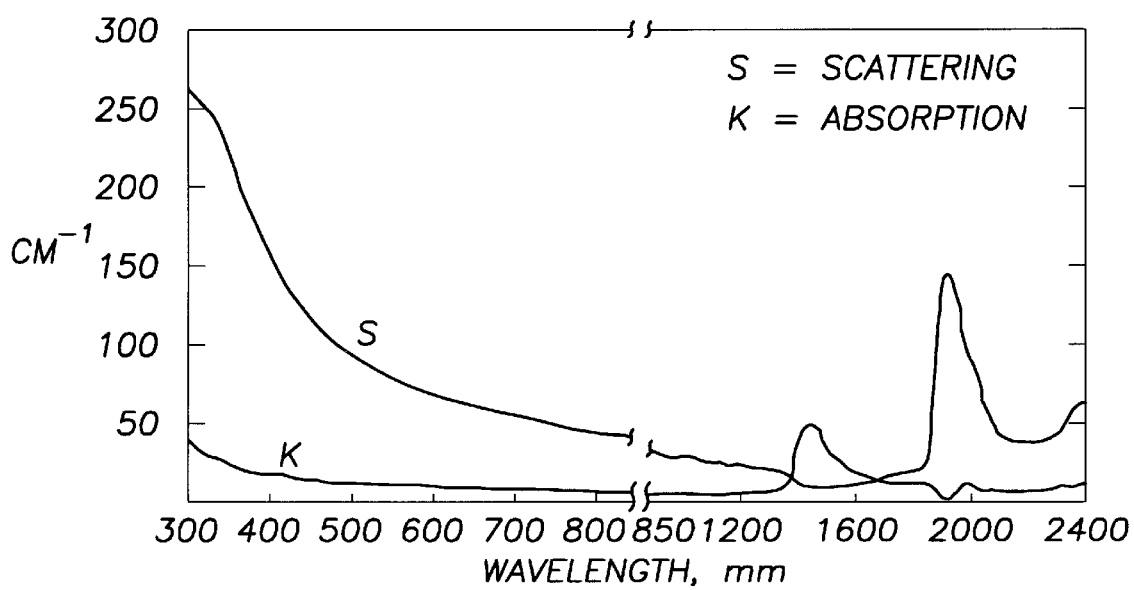
FIG. 2 illustrates the inverse relationship between optical scattering and wavelength.

The stratum corneum and epidermis provide an optical barrier primarily by absorption of radiation and to a lesser degree, by optical scattering. The dermis has distinctly different optical properties than the epidermis, reflecting differences in structure and composition. The dermal region may be considered a turbid tissue matrix in which optical scattering is an inverse function of wavelength and largely defines the depth of optical penetration for a non-absorptive wavelength. FIG. 2 illustrates the inverse relationship between optical scattering and wavelength.

Scattering results from inhomegeneities in a medium's refractive index, corresponding to physical inhomogenetics. The spatial distribution and intensity of scattered light depends upon the size and shape of the inhomogeneities relative to the wavelength, and upon the difference in refractive index between the medium and inhomogeneities. Thus, microstructures (e.g. collagen fibrils) in the dermis largely determine the penetration depth at various wavelengths. For example, at shorter wavelengths, the wavelength has dimensions of the same order as the collagen fibers. As a result, scattering is strong and the penetration depth is correspondingly reduced.

The present invention employs lasers with wavelengths in the near-infrared portion of the electromagnetic spectrum (700 to 1400 nm) to limit scattering in the dermal region so that the radiation can reach the treatment site.

Figure 3:
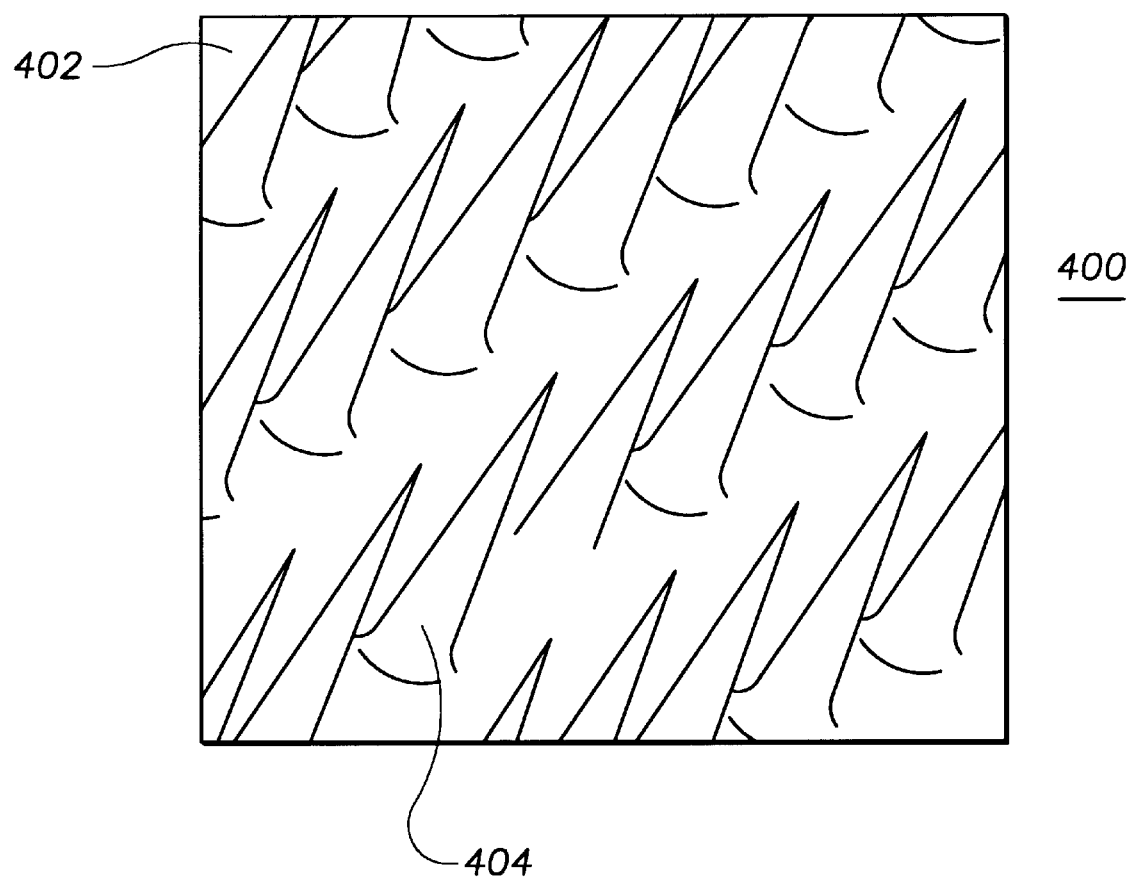
FIG. 3 is an electron microscope image of a micro-needle array.

Heat generation at the treatment site is enhanced through micro-poration techniques wherein micropores are created in the stratum corneum. Such micropores serve as channels for any fluid media needing to be introduced into the site. Microporation can be achieved using a micro-needle patch. FIG. 3 illustrates a sectional view 400 of micro-needle 404 on micro-needle patch 402 enlarged by an electron microscope. Micro-needles 404 on micro-needle patch 402 can be placed onto the treatment area and the bio-compatible fluid passed through micro-needles 404 directly into the tissue. Conversely, micro-needles 404 on micro-needle patch 402 can be placed onto the treatment area to form micropores in the tissue. Micro-needles 404 on micro-needle patch 402 are then removed from the area. The micropores remain for a period. Fluids can be administered by capillary action and preferably along a pressure gradient through the micropores and into the treatment tissue. As a result, the user will be able to achieve more uniform, enhanced heating over a relatively large treatment area.

Micro-needles on a single patch generally have the same dimensions. Typically, each needle is approximately 40–50 $\mu$m in length and has a diameter (at the base of the needle—where the needle is attached to the patch) of approximately 12–15 $\mu$m.

Figure 4:
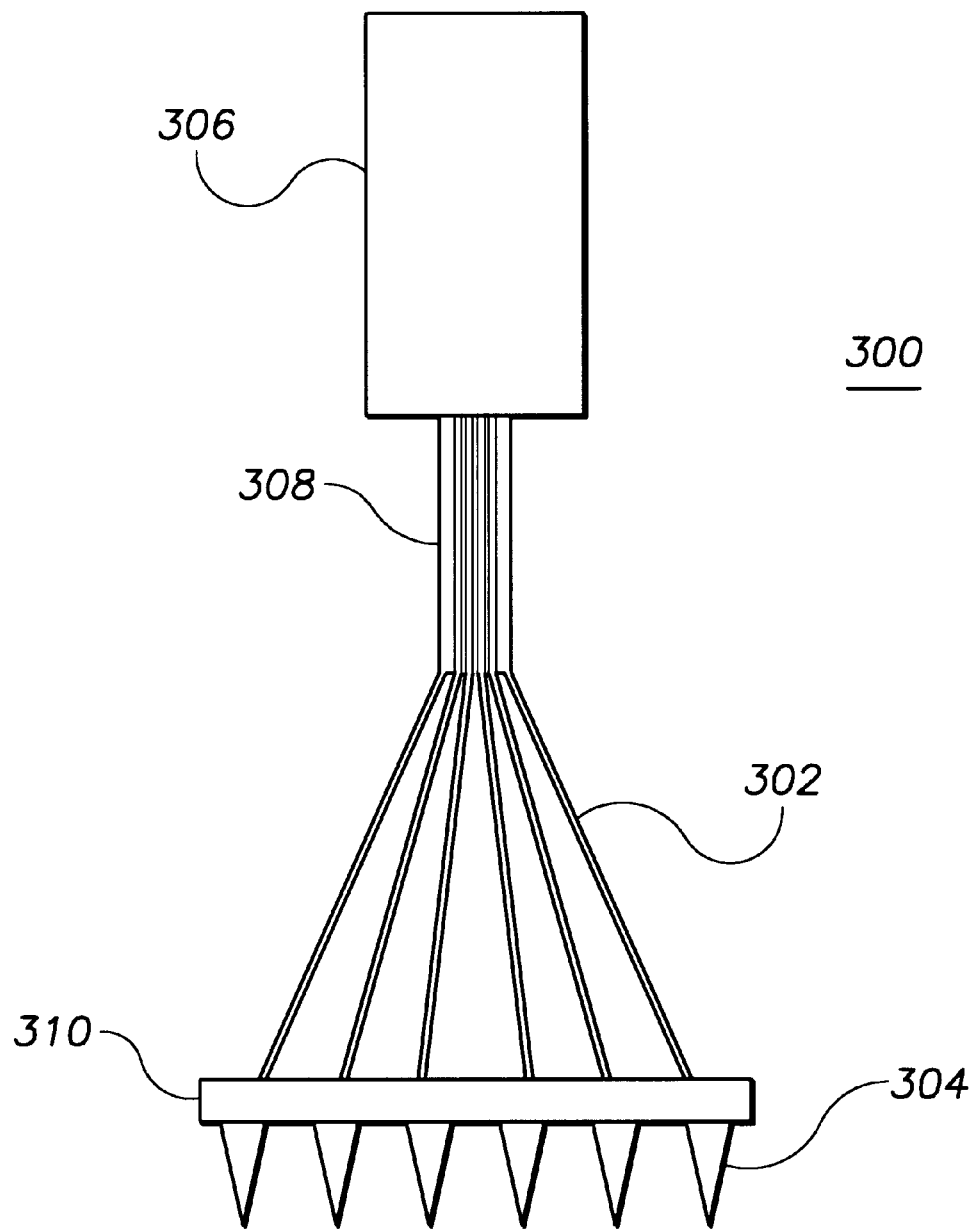
FIG. 4 is a diagram of the laser radiation delivery system.

Radiation is then applied to the treatment site. In turn, micro-needles can be employed to enhance heat generation at the treatment site during irradiation to achieve and sustain a critical core temperature necessary to is ablate or stimulate the treatment area. Illustrated in FIG. 4 is laser radiation delivery system 300 where the proximate end of multiple fibers 302 is connected to laser 306 via fiber bundle 308. Multiple fibers 302 are inserted into micro-needles 304 that are arranged in an array on micro-needle patch 310. Micro-needles 304 facilitate radiation delivery through the epidermis by providing a painless way for the optical fibers to cross the stratum corneum and to facilitate the transmission of radiation through the epidermis.

Figure 5:
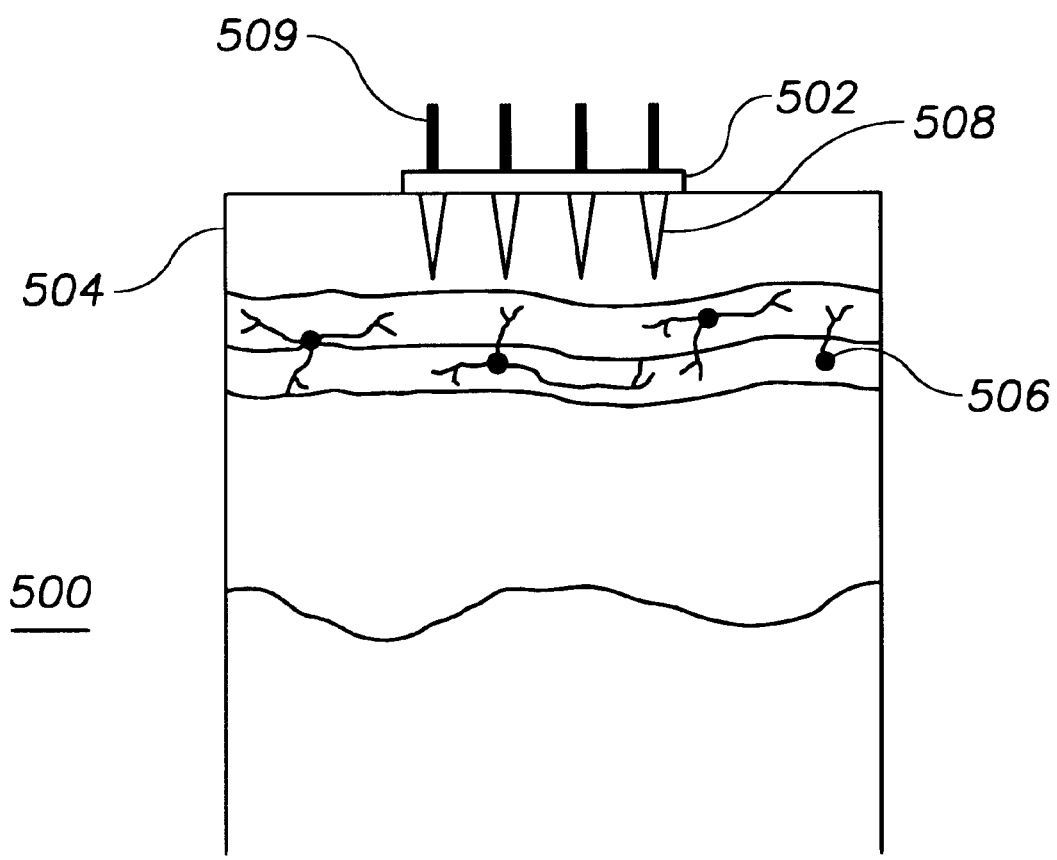
FIG. 5 is a schematic illustration of the laser radiation delivery system being employed on a cross-section of tissue.

In an example and preferred embodiment, the present invention may be used to treat vascular lesions. According to FIG. 2, a 980 nm diode laser would be preferable to limit scattering in the dermal region so that the radiation can reach the treatment site. Additionally, U.S. Pat. No. 5,749,868 teaches that near infrared light achieves enhanced selectivity in the treatment of vascular lesions. While 980 nm light limits scattering in the dermal region to achieve an increased penetration depth, heat generation at the treatment site is not uniform over large treatment areas and may be inadequate to achieve and maintain the critical core temperature that is necessary to ablate or stimulate. Therefore, a micro-needle patch is applied prior to laser therapy to enhance heat generation at the treatment site and to provide for uniform heating over a relatively large surface area. For example, FIG. 5 illustrates application of a device to treatment area 500. Micro-needles 508 on micro-needle patch 502 cross stratum corneum 504, but do not strike nerve endings 506 therefore the procedure is painless because nerve endings 506 are not pierced. Micro-needles 508 act like little tunnels that go through stratum corneum 504, through which optical fibers 509 may be passed. A scattering fluid is injected into the tissue. The scattering fluid can be followed by a dispersion fluid to aid in pushing the scattering fluid to the treatment site. The dispersion fluid is optically transparent to the treatment wavelength involved to prevent any interference with the radiation delivery.

A micro-needle patch enhances heat generation at the treatment site by injecting a bio-compatible, medium-viscous to highly-viscous fluid into the tissue that will essentially scatter light only at the treatment site to achieve and sustain the critical core temperature that is necessary to ablate the vessels. Alternatively, another micro-poration technique may be used to introduce the fluid.

In an embodiment, the optically transparent fluid is composed of 80% glycerine and 20% water and the light-scattering fluid is composed of oil and water with 1 to 5 parts oil in a 100-part mixture. One of ordinary skill in the art, in light of the teachings herein, can readily use various scattering material and diluents without exceeding the scope of the present invention. For example, fat emulsions that contain soybean oil, egg, phospholipids and glycerol such as Intralipid, Nutralipid, or Liposyn can be used without departing from the scope of the invention.

As another example, isotonic phosphate buffer saline may be used as the diluent instead of deionized $H_2O$ without departing from the scope of the invention.

The laser may then be employed to stimulate or ablate the treatment site. The laser's light penetrates the epidermis then travels to the treatment site where the photons of the laser radiation are scattered in the quasi absorption-free scattering fluid and then deposited into the tissue to enhance heat generation at the treatment site and to obtain a uniform heating result across a relatively large treatment site.

One of ordinary skill in the art, in light of the teachings herein, can readily use this method in the treatment of varicose veins or other vascular lesions without departing from the scope of the present invention. For example in varicose vein therapy, longer wavelengths are useful to penetrate more deeply to reach the treatment site. A micro-needle patch then may be employed to enhance heat generation at the treatment site and to obtain heating uniformity over a large surface area.

Figure 6:
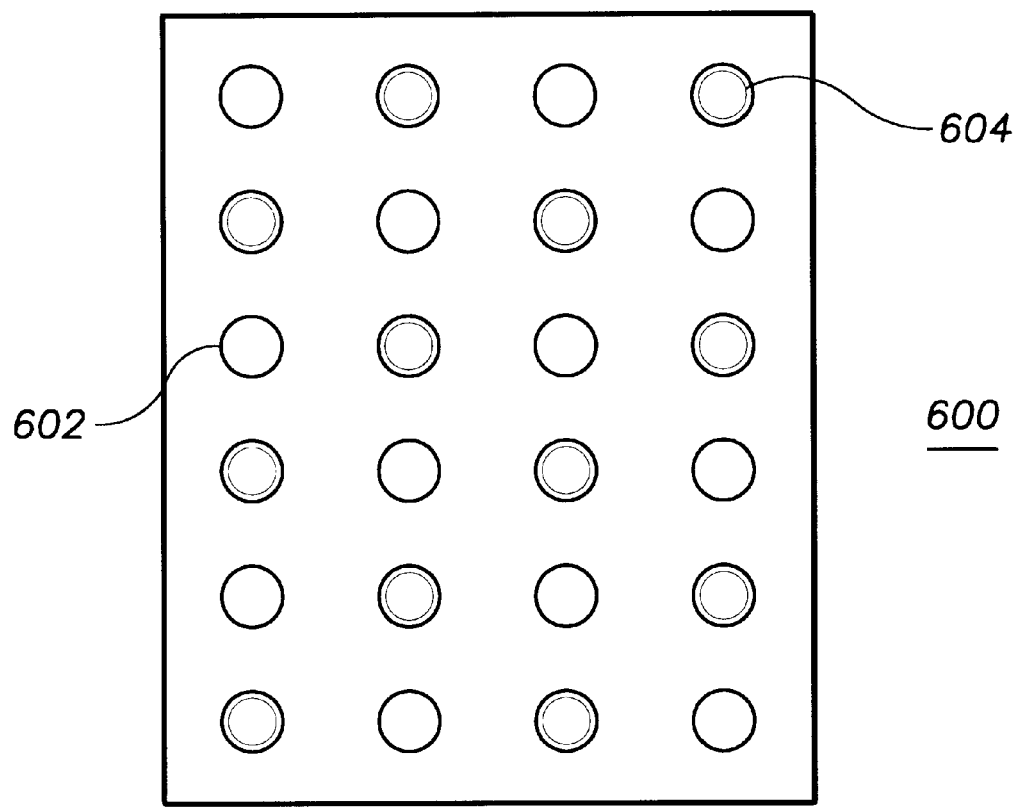
FIG. 6 illustrates a micro-needle array incorporating both laser energy and fluid delivering needles on the same patch.

FIG. 6 illustrates a top view of micro-needle patch 600. This particular version of the present invention incorporates both laser delivery 'needles' 604 and scattering-fluid delivery 'needles' 602 on the same patch. This embodiment allows users to administer a complete treatment using the same patch, thereby reducing treatment time and complexity. The practitioner simply applies a single micro-needle patch, administers the scattering fluid, and then the laser radiation. Further, this variation ensures that scattering fluid is administered precisely at the site of laser delivery.

Figure 7:
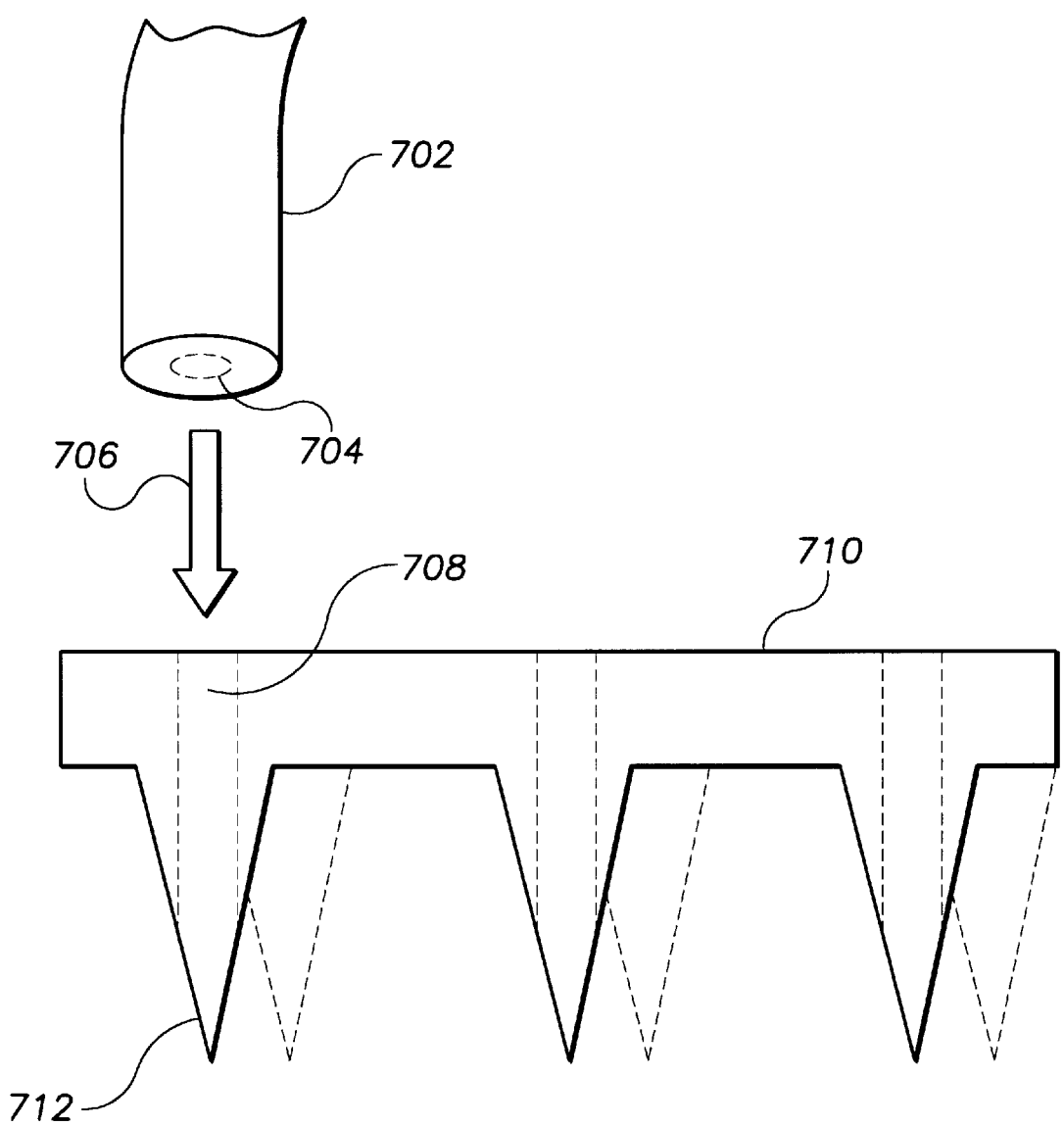
FIG. 7 illustrates a system for coupling laser energy from an optical fiber into a micro-needle patch.

FIG. 7 illustrates a variation of the present invention wherein micro-needle patch 710 containing micro-needles 712 is manufactured out of an optically transparent material such as quartz glass. Within needles 712 is a region with a variant refractive index that comprises 'core' 708. Fibers 702 are properly oriented and attached 706 to needles 712 such that fiber core 704 aligns with needle 'core' 708. Laser energy can then be administered transdermally from optical fiber 702, through needles 712, and into the treatment site. Conversely, a radiation source may be placed directly onto the micro-needle patch for delivery into the tissue, wherein the needle 'core' 708 captures and transmits light across the stratum corneum.

In another example and preferred embodiment, the present invention may be used in non-ablative facial rhytide treatment. A 1.32 $\mu$m laser may be employed to selectively injure the lower papillary/upper reticular dermis to stimulate the skin to produce new collagen and "remodel" itself, thereby de-emphasizing wrinkles. According to FIG. 2, scattering in the dermis is minimal at the 1.32 $\mu$m wavelength.

A micro-needle patch may then be employed to inject a scattering fluid into the tissue to scatter the radiation only at the treatment site to achieve a uniform heating effect. A uniform heating effect is especially advantageous in facial rhytide therapy where the treatment area is particularly large. Additionally, the scattering fluid enhances heat generation at the treatment site, therefore an increase in power is not necessary to stimulate the lower papillary/upper reticular dermal region and the risk of injury to the epidermal barrier is significantly reduced. The holes that are created in the stratum corneum by the micro-needles may provide an additional means to reduce the risk of thermal injury because the holes may release some of the residual heat that has built up within the tissue underlying the stratum corneum in the course of laser therapy.

Certain changes may be made in the above constructions without departing from the scope of the invention, it is intended that all matter contained in the above description and shown in the accompanying drawings be considered as illustrative and not in a limiting sense. For example, a desired energy choice may include, but is not limited to non-coherent radiation, radiation from flashlamps, diodes, frequency doubled laser diodes, laser diode pumped lasers, or photoluminescent diodes without departing from the scope of this invention.

As another example, although most references cite to an epidermal barrier that must be penetrated, the use of stratum corneum in the above-stated examples should not be taken to imply that the present invention is limited to enhancing radiation delivery through the epidermis. The present invention may be used to enhance radiation delivery through any inner or outer barrier that is encountered. Other suitable variations of the present invention may include, but are not limited to delivering laser energy through soft tissue in the oral cavity or through arterial walls.

Having described the preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A therapeutic laser delivery system for the improved transbarrier delivery of laser radiation across a biological barrier layer protecting a treatment site with improved uniformity of dispersion comprising:

a laser radiation source;

means for painlessly generating a multitude of newly formed micro pores in said biological barrier layer;

means for delivering a bio-compatible, transparent, light-scattering fluid to said treatment site;

means for optically connecting said laser radiation source to said newly formed micro pores; and wherein said newly formed micro pores provide access to said treatment site for radiation from said laser radiation source.

2. A transbarrier, therapeutic laser delivery system according to claim 1, wherein said means for painlessly generating a multitude of newly formed micro pores in a biological barrier layer is a micro-needle patch, comprising a multitude of micro-needles.

3. A transbarrier, therapeutic laser delivery system according to claim 2, wherein said laser radiation source is coupled to said newly formed micro pores by an optical fiber bundle comprised of individual fibers, wherein said individual fibers are associated with at least one said newly formed micro pore.

4. A transbarrier, therapeutic laser delivery system according to claim 1, wherein said laser radiation source is coupled to said newly formed micro pores by an optical fiber bundle such that individual fibers are associated with at least one said newly formed micro pore.

5. A transbarrier, therapeutic laser delivery system according to claim 1, further comprising an optically transparent, bio-compatible dispersion fluid composed of 80% glycine and 20% water, wherein said dispersion fluid aids in pushing said light-scattering fluid to said treatment area.

6. A transbarrier, therapeutic laser delivery system according to claim 1, wherein said bio-compatible, transparent, light-scattering fluid is composed of oil and water, with about 1 to 5 parts oil in a 100-part mixture.

7. A transbarrier, therapeutic laser delivery system according to claim 2, wherein a single micro-needle patch, containing an array of micro-needles, is attached to both said laser radiation source and said fluid source whereby said fluid and said radiation are delivered in a simultaneous manner.

8. A transbarrier, therapeutic laser delivery system according to claim 2, wherein said micro-needle patch is optically transparent to said laser radiation, whereby optical fibers or said laser radiation source may be optically coupled to said micro-needle patch at a base of each said micro-needle.

9. A method of using the transbarrier, therapeutic laser delivery system according to claim 1, comprising placing said laser radiation source over said multitude of newly formed micro pores such that radiation from said laser radiation source is transmitted through said newly formed micro pores to said treatment site.

10. A method of using the transbarrier, therapeutic laser delivery system according to claim 2, comprising the step of administering said bio-compatible scattering fluid and a bio-compatible dispersion fluid to said treatment site through a pre-treatment micro-needle patch, which is removed prior to commencement of laser treatment with said micro-needle patch.

11. A method for improving the delivery of laser radiation for transbarrier therapeutic treatments comprising the steps of:

applying a micro poration technique to painlessly create a multitude of newly formed micro pores in a biological barrier protecting a treatment site;

injecting a bio-compatible, light-scattering fluid, capable of dispersing therapeutic radiation, through said multitude of newly formed micro pores into a tissue around said treatment site;

delivering said therapeutic radiation from a source to said treatment site through a suitable means and said multitude of newly formed micro pores; and scattering said therapeutic radiation at said treatment site to promote improved uniformity and enhanced density of said radiation at said treatment site.

12. A method for improved delivery of laser radiation for transbarrier therapeutic treatments according to claim 11, wherein said applied micro poration technique is an application of a micro-needle patch.

13. A method for improved delivery of laser radiation for transbarrier therapeutic treatments according to claim 11, wherein said suitable means for delivery of therapeutic radiation is an optical fiber bundle optically connecting said radiation source to said newly formed micro pores.

14. A method for improved delivery of laser radiation for transbarrier therapeutic treatments according to claim 11, wherein said bio-compatible light-scattering fluid is composed of oil and water, with about 1 to 5 parts oil in a 100-part mixture.

15. A method for improved delivery of laser radiation for transbarrier therapeutic treatments according to claim 11, wherein said light-scattering, bio-compatible fluid is injected into said tissue through a micro-needle patch.

16. A method for improved delivery of laser radiation for transbarrier therapeutic treatments according to claim 11, wherein an optically transparent, bio-compatible dispersion fluid is administered after said light-scattering, bio-compatible fluid to disperse said light-scattering, bio-compatible fluid evenly throughout said treatment site.

17. A method for improved delivery of laser radiation for transbarrier therapeutic treatments according to claim 11, wherein said laser radiation is administered to said treatment site through a second micro-needle patch.

18. A method for improved delivery of laser radiation for transbarrier therapeutic treatments according to claim 11, wherein said laser radiation and said light-scattering, bio-compatible fluid are delivered through a same said micro-needle patch.

* * * * *